（12） United States Patent
Haran et al.

(10) Patent No.: US 8,753,007 B2
(45) Date of Patent: Jun. 17, 2014

(54) FUEL CLOUD POINT OR FREEZE POINT SENSOR WITH COLLINEAR OPTICAL GEOMETRY

(75) Inventors: Frank M. Haran, North Vancouver (CA); Sebastien Tixier, North Vancouver (CA); Stuart J. Heath, Surrey (CA)

(73) Assignee: Honeywell ASCa Inc., Ontario (CA)

( * ) Notice: Subject to any disclaimer, the term of this patent is extended or adjusted under 35 U.S.C. 154(b) by 888 days.

(21) Appl. No.: 12/857,863

(22) Filed: Aug. 17, 2010

(65) Prior Publication Data

US 2012/0044968 A1    Feb. 23, 2012

(51) Int. Cl.
 G01N 25/00    (2006.01)
 G01K 1/00    (2006.01)
 G01J 5/00    (2006.01)
(52) U.S. Cl.
 USPC ............................ 374/18; 374/120; 374/130
(58) Field of Classification Search
 USPC .......................................... 374/18, 120, 130
 See application file for complete search history.

(56) References Cited

U.S. PATENT DOCUMENTS

| | | | | |
|---|---|---|---|---|
| 4,519,717 | A | | 5/1985 | Jones et al. |
| 4,946,288 | A | * | 8/1990 | Siska et al. ...................... 374/20 |
| 5,007,733 | A | | 4/1991 | Laurent et al. |
| 5,088,833 | A | | 2/1992 | Tsang et al. |
| 5,090,817 | A | | 2/1992 | Ker et al. |
| 5,460,450 | A | * | 10/1995 | Buck ............................... 374/20 |
| 5,615,954 | A | * | 4/1997 | Nishizawa et al. .............. 374/17 |
| 5,641,230 | A | | 6/1997 | Okubo |
| 5,651,614 | A | | 7/1997 | Juneau |
| 5,708,196 | A | | 1/1998 | Tolvanen et al. |
| 5,971,609 | A | * | 10/1999 | Kijima et al. .................... 374/17 |
| 6,076,959 | A | | 6/2000 | Nagasawa |
| 6,817,754 | B2 | | 11/2004 | Tsang et al. |
| 6,827,484 | B2 | | 12/2004 | Tsang et al. |
| 6,966,692 | B2 | | 11/2005 | Tsang et al. |
| 7,581,877 | B1 | * | 9/2009 | Zarrabian ....................... 374/16 |
| 2003/0193989 | A1 | * | 10/2003 | Tsang et al. .................... 374/16 |

(Continued)

FOREIGN PATENT DOCUMENTS

FR    2206001 A5    5/1974
GB    1438754 A    6/1976

OTHER PUBLICATIONS

Sebastien Tixier, "Standard Test Method for Cloud Point of Petroleum Products (Constant Cooling Rate Method)", ASTM International, Aug. 5, 2010, 7 pages.

(Continued)

*Primary Examiner* — Mirellys Jagan

(57) ABSTRACT

A system includes a sensing cell having a walled structure configured to receive a fuel sample within an interior space of the walled structure. The sensing cell also has at least one cooling surface located on at least a portion of the walled structure and configured to cool the fuel sample. The sensing cell further has an optical port configured to couple to one or more optical fibers and to provide first radiation to the fuel sample. In addition, the sensing cell has a mirror configured to reflect the first radiation in order to provide second radiation to the optical port. The optical port defines a collinear optical geometry for providing the first radiation to the fuel sample and receiving the second radiation through the fuel sample. The system also includes at least one cooler configured to cool the fuel sample in the sensing cell by cooling the at least one cooling surface.

14 Claims, 4 Drawing Sheets

(56) References Cited

U.S. PATENT DOCUMENTS

2005/0053116 A1* 3/2005 Tsang et al. .................. 374/20
2005/0220166 A1* 10/2005 Kanai et al. .................. 374/16
2006/0098708 A1* 5/2006 Cleris et al. .................. 374/16
2010/0012410 A1* 1/2010 Pryor et al. ................. 180/69.4
2012/0287961 A1* 11/2012 Sakami ........................ 374/28

OTHER PUBLICATIONS

Supplementary European Search Report dated Nov. 28, 2013 in connection with European Patent Application No. EP 11 81 7603.

* cited by examiner

FUEL CLOUD POINT OR FREEZE POINT SENSOR WITH COLLINEAR OPTICAL GEOMETRY

TECHNICAL FIELD

This disclosure relates generally to fuel sensors. More specifically, this disclosure relates to a fuel cloud point or freeze point sensor with collinear optical geometry.

BACKGROUND

Diesel fuel, jet fuel, and other types of fuel are often manufactured or processed to have a specified cloud point or freeze point. The cloud point of a fuel denotes the temperature at which the first solidified wax particles form within the fuel as the temperature of the fuel decreases. The freeze point of a fuel denotes the temperature at which, after solidified wax particles have formed, the last solidified wax particles melt as the temperature of the fuel increases.

Traditional cloud point and freeze point measurements often use changes in optical scattering characteristics of a fuel as the temperature of the fuel is adjusted. However, conventional sensors often times require access to two sides of a fuel sample. This may be difficult or impossible in confined spaces. If access is limited to one side, a reflecting path can be used. Unfortunately, the refractive index of fuel is temperature-dependent, which can lead to misalignment.

SUMMARY

This disclosure provides a fuel cloud point or freeze point sensor with collinear optical geometry.

In a first embodiment, an apparatus includes a walled structure configured to receive a fuel sample within an interior space of the walled structure. The apparatus also includes at least one cooling surface located on at least a portion of the walled structure and configured to cool the fuel sample. The apparatus further includes an optical port configured to couple to one or more optical fibers and to provide first radiation to the fuel sample. In addition, the apparatus includes a mirror configured to reflect the first radiation in order to provide second radiation to the optical port. The optical port defines a collinear optical geometry for providing the first radiation to the fuel sample and receiving the second radiation through the fuel sample.

In a second embodiment, a system includes a sensing cell having a walled structure configured to receive a fuel sample within an interior space of the walled structure. The sensing cell also has at least one cooling surface located on at least a portion of the walled structure and configured to cool the fuel sample. The sensing cell further has an optical port configured to couple to one or more optical fibers and to provide first radiation to the fuel sample. In addition, the sensing cell has a mirror configured to reflect the first radiation in order to provide second radiation to the optical port. The optical port defines a collinear optical geometry for providing the first radiation to the fuel sample and receiving the second radiation through the fuel sample. The system also includes a cooler configured to cool the fuel sample in the sensing cell by cooling the at least one cooling surface.

In a third embodiment, a method includes receiving a fuel sample in a sensing cell. The method also includes providing first radiation to the fuel sample in the sensing cell and reflecting the first radiation that has interacted with the fuel sample off a mirror of the sensing cell. The method further includes receiving the reflected first radiation that has again interacted with the fuel sample as second radiation. The first radiation is provided and the second radiation is received using a collinear optical geometry. In addition, the method includes determining at least one of a cloud point and a freeze point of the fuel sample using measurements of the second radiation.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 7, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
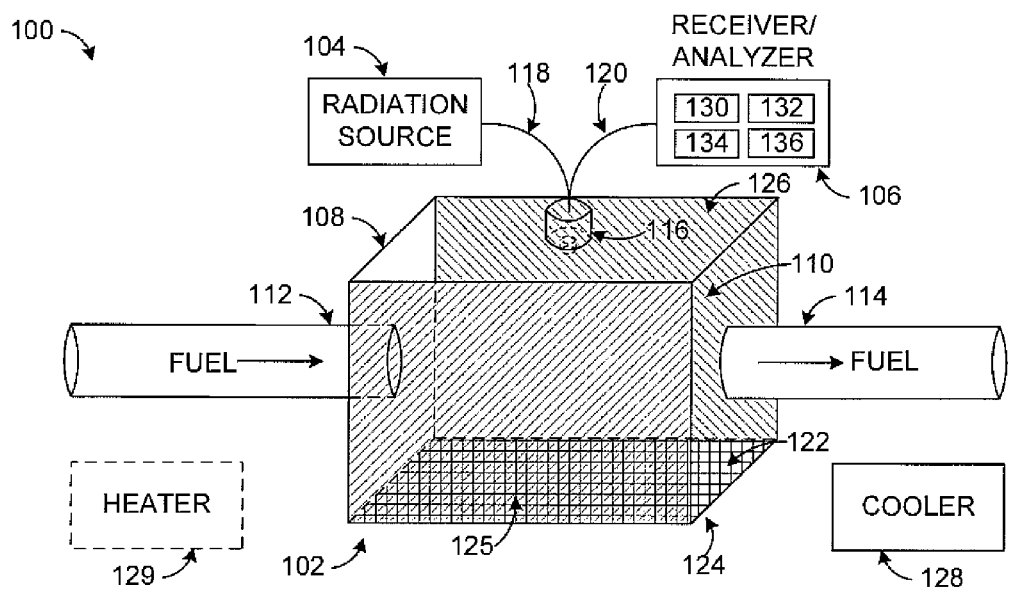
FIG. 1 illustrates an example fuel cloud point or freeze point sensing system according to this disclosure.

FIG. 1 illustrates an example fuel cloud point or freeze point sensing system 100 according to this disclosure. As shown in FIG. 1, the sensing system 100 includes a sensing cell 102, a radiation source 104, and a receiver/analyzer 106.

In general, the sensing cell 102 receives a sample of a fuel, such as a petroleum-based fuel (like diesel or jet fuel) or a biomass-based fuel (such as biodiesel or biojet fuel). The sensing cell 102 cools and optionally heats the fuel sample in order to measure the cloud point or freeze point of the fuel. As noted above, the cloud point of a fuel denotes the temperature at which the first solidified wax particles form within the fuel as the temperature of the fuel decreases. The freeze point of a fuel denotes the temperature at which, after solidified wax particles have formed, the last solidified wax particles melt as the temperature of the fuel increases. The radiation source 104 provides optical radiation (such as visible light) to the sensing cell 102. The receiver/analyzer 106 receives and measures radiation that has interacted with the fuel sample and processes the measurements to identify the cloud point or freeze point of the fuel sample.

In this example embodiment, the sensing cell 102 includes a walled structure 108 defining an internal volume or space 110. A fuel sample enters the sensing cell 102 via an inlet 112 and exits the sensing cell 102 via an outlet 114. In this particular example, the walled structure 108 has a generally rectangular cross-section, and the inlet 112 and the outlet 114 are located on opposite sides of the walled structure 108. However, the walled structure 108 could have any other suitable size and shape, and the inlet 112 and the outlet 114 could have any suitable locations into and out of the walled structure 108. In some embodiments, the walls of the structure 108 can be insulated to help cool and/or heat the fuel sample within the walled structure 108.

The sensing cell 102 also includes an optical port 116, which is coupled to one or more optical fibers 118-120. The optical port 116 allows radiation from the radiation source 104 to travel into the walled structure 108, where the radiation is reflected off a mirror 122. The optical port 116 also allows the radiation reflected off the mirror 122 to be provided to the receiver/analyzer 106. The optical port 116 includes any suitable structure that can be coupled to one or more optical fibers.

In this example, at least one optical fiber 118 couples the radiation source 104 to the optical port 116, and at least one optical fiber 120 couples the receiver/analyzer 106 to the optical port 116. The optical fibers 118-120 could have any suitable arrangement. For example, the optical fibers 118-120 could form part of a bifurcated fiber that allows radiation from the radiation source 104 to be provided to the sensing cell 102 and that can provide reflected radiation from the sensing cell 102 to the receiver/analyzer 106. The optical fibers 118-120 could also represent a fiber bundle having multiple fibers packaged close together. In particular implementations, the optical fiber 118 could be in the middle of the fiber bundle, and multiple optical fibers 120 could be arranged around the optical fiber 118. In still other embodiments, the optical fibers 118-120 could represent a double-clad optical fiber. Any other suitable optical fiber(s) in any suitable configuration could be used in the sensing system 100.

The mirror 122 reflects radiation from the optical port 116, which causes the radiation to traverse multiple paths through the sensing cell 102 (one from the optical port 116 to the mirror 122, and one from the mirror 122 to the optical port 116). Note that these paths may partially or completely overlap depending on the configuration of the sampling cell 102. The mirror 122 represents any suitable structure that is substantially reflective to at least the radiation provided by the radiation source 104. In this particular example, the optical port 116 is located on top of the sensing cell 102, and the mirror 122 is located on at least a portion of the bottom of the sensing cell 102. However, the optical port 116 and the mirror 122 could be located in any other suitable positions.

The sensing cell 102 further includes one or more cooling surfaces. In this example, the sensing cell 102 includes three cooling surfaces 124-126. The cooling surface 124 is located on at least a portion of the bottom mirrored surface of the walled structure 108. The cooling surface 125 is located on at least a portion of the front surface of the walled structure 108. The cooling surface 126 is located on at least a portion of the back surface of the walled structure 108. However, each cooling surface could include any portion of any surface of the sensing cell 102. Moreover, less than two or more than three cooling surfaces could be used in the sensing cell 102.

The cooling surfaces 124-126 in FIG. 1 are thermally coupled to at least one cooler 128. The cooler 128 can cool the surfaces 124-126 in order to decrease the temperature of the fuel sample within the sensing cell 102. Any suitable cooling mechanism could be used to cool the fuel sample in the sensing cell 102, and any suitable number of coolers 128 could be used. For example, multiple double-stage Peltier coolers could be used with multiple cooling surfaces 124-126 to cool the fuel sample. The cooler 128 could also represent a cryogenic cooler, such as a sterling cryo-cooler having a cryogenic fingertip that contacts a single cooling surface 124-126 to cool the fuel sample. The cooler(s) 128 could operate using any suitable number of cooling surfaces. Optionally, a warmer 129 can warm one or more surfaces of the walled structure 102 in order to increase the temperature of the fuel sample within the sensing cell 102. The warmer 129 includes any suitable structure for warming a fuel sample.

The radiation source 104 includes any suitable structure for providing radiation at one or more desired wavelengths or wavelength bands. The radiation source 104 could, for example, include one or more light emitting diodes (LEDs) that emit light at the appropriate wavelength(s) or wavelength band(s).

The receiver/analyzer 106 includes any suitable structure for receiving and analyzing radiation that has interacted with the fuel sample in the sensing cell 102. For example, the receiver/analyzer 106 could include a detector 130 that measures one or more characteristics of the radiation that has interacted with the fuel sample. The detector 130 could represent a photodetector, spectrometer, or other detection mechanism. The receiver/analyzer 106 could also include a processing unit 132 that analyzes the measurements obtained by the detector 130 to determine the cloud point or freeze point of the fuel sample. The processing unit 132 could include a microprocessor, microcontroller, digital signal processor (DSP), field programmable gate array (FPGA), application specific integrated circuit (ASIC), or other processing device. The receiver/analyzer 106 could further include a memory unit 134 that stores instructions and data used, generated, or collected by the processing unit 132. The memory unit 132 could include any suitable volatile and/or non-volatile storage and retrieval device(s). In addition, the receiver/analyzer 106 could include an interface 136 for transmitting data (such as determined cloud points or freeze points) to an external device or system. The interface 136 could represent any suitable wired or wireless interface, such as an Ethernet interface.

In one aspect of operation, the sensing cell 102 receives a fuel sample, which can be provided in any suitable manner. For instance, the fuel sample can be pumped into the sensing cell 102 via the inlet 112. The fuel sample within the sensing cell 102 could be trapped within the sensing cell 102, such as by using valves to seal the inlet 112 and the outlet 114. Alternatively, a pump or other device supplying the fuel sample to the sensing cell 102 can be turned off so that the fuel sample within the sensing cell 102 generally stays within the sensing cell 102.

Once the fuel sample is within the sensing cell 102, the sensing cell 102 begins lowering the temperature of the fuel sample using the cooler 128, radiation from the radiation source 104 passes through the fuel sample, and the receiver/analyzer 106 analyzes the radiation that interacts with the fuel sample. As the temperature of the fuel sample falls, solidified wax particles form in the fuel and can be detected by the receiver/analyzer 106. The receiver/analyzer 106 can therefore identify the cloud point of the fuel sample. The receiver/analyzer 106 could also warm the fuel sample after the wax particles have formed, either by turning off the cooler 128 or using the warmer 129. The increasing temperature causes the solidified wax particles to melt, which can be detected by the receiver/analyzer 106. The receiver/analyzer 106 can therefore identify the freeze point of the fuel. Depending on the implementation, the receiver/analyzer 106 could determine the cloud point of the fuel, the freeze point of the fuel, or both.

The temperature of the fuel sample in the sensing cell 102 can be determined by the receiver/analyzer 106 so that the measurements of the radiation that has interacted with the fuel sample can be associated with specific temperatures. The temperature of the fuel sample in the sensing cell 102 can be determined in any suitable manner. For example, the temperature of the fuel sample in the sensing cell 102 can be determined based on the temperature setting of the cooler 128. The receiver/analyzer 106 could also receive temperature measurements from a temperature sensor located within the sensing cell 102 or mounted on one of the cooling surfaces 124-126. Any other suitable technique could be used to determine the temperature of the fuel sample within the sensing cell 102.

Once the cloud point or freezing point of the fuel sample has been determined, the fuel sample in the sensing cell 102 can be flushed, such as by pumping or otherwise providing new fuel through the inlet 112. The new fuel provided during flushing can warm the sensing cell 102, and the process of determining the cloud point or freeze point can be repeated using a new fuel sample.

This type of sensing system 100 can provide various advantages depending on the implementation. For example, one drawback of conventional sensors is the large size of their measurement cells. Their size typically requires the use of larger sensor enclosures and coolers, resulting in higher costs. Also, dissipating high heat loads in these conventional sensors often requires the use of cooling water or forced air. In contrast, the sensing system 100 can use one optical port 116 and a mirror 122 to yield a double pass cell, meaning radiation follows two paths through the fuel (from the port 116 to the mirror 122 and back to the port 116). Using this type of folded cell means that the cell 102 can be half the size for a given interaction length, requiring less cooling power and lowering measurement time. In fact, the sensing cell 102 could allow the cooler 128 to simply dissipate heat through passive elements (such as radiative heat sinks or natural convection), rather than cooling water or forced air. Also, optical access is needed at only one side of the sensing cell 102 (the top in this example), which can further reduce the size of the sensing cell 102. The remaining sides can be used for sample transport and for cooling/insulation, and fewer optical ports can help improve cell insulation since there are fewer openings for heat entry or escape. Further, because the optical fibers 118-120 are collinear, their geometry is substantially insensitive to opto-mechanical effects and bulk refractive index changes. In addition, this configuration enables the use of optical fibers to locate the radiation source 104 and the receiver/analyzer 106 remotely from the sensing cell 102, allowing the sensing cell 102 to be placed in more demanding, hostile locations. This can be quite useful, for instance, when the sensing cell 102 is exposed to moisture condensation due to low temperatures, fuel vapors, and vibrations from a cryogenic cooler.

The sensing system 100 can be used in any suitable environment. For example, the sensing system 100 can be used in a manufacturing environment where a fuel is being produced, such as an oil refinery or a biofuel production system. In particular embodiments, the cloud point or freeze point of a fuel being produced can be output by the receiver/analyzer 106 to a process controller, which can use the cloud point or freeze point to adjust the manufacturing process. The sensing system 100 could also be used in an environment where fuel is being processed, transported, or used, such as when the sensing system 100 is used to verify that fuel has an appropriate cloud point or freeze point. The sensing system 100 can be used in any other suitable environment.

Figure 2:
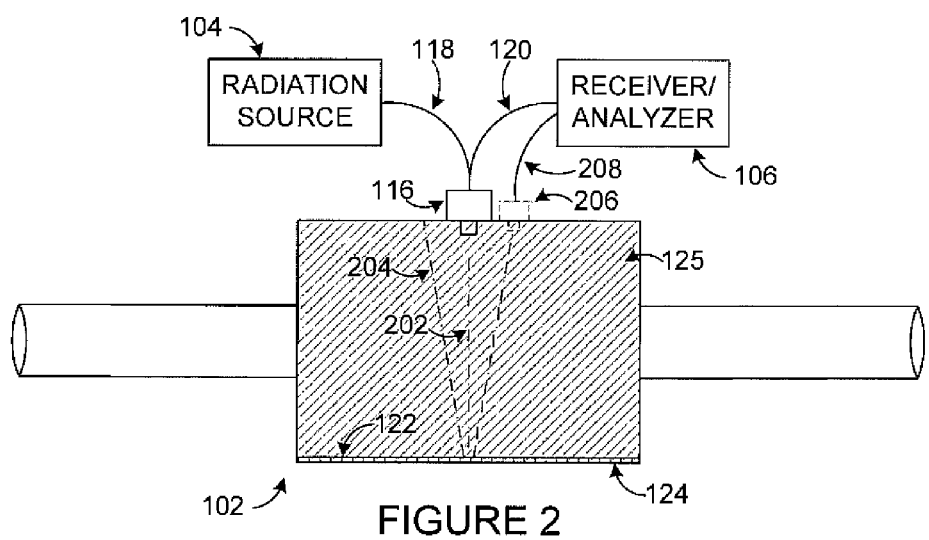
FIG. 2 illustrates a side view of the example fuel cloud point or freeze point sensing system of FIG. 1 according to this disclosure.

FIG. 2 illustrates a side view of the example fuel cloud point or freeze point sensing system 100 of FIG. 1 according to this disclosure. As shown in FIG. 2, radiation from the radiation source 104 can follow an optical path 202 between the optical port 116 and the mirror 122. The optical path 202 is shown here as being substantially linear. That is, radiation from the optical port 116 travels along a substantially linear path to the mirror 122 and then back to the optical port 116 over the same substantially linear path. This may represent the path that most of the radiation traverses when there are little or no wax particles in the fuel sample. However, the formation of wax particles in the fuel sample may cause the radiation to follow a more diverged path 204.

A measurement of the radiation along the path 202 may be referred to as a specular signal measurement. These measurements can be obtained by measuring the radiation received at the optical port 116. Also, a measurement of the radiation along the path 204 may be referred to as a diffuse signal measurement. Those measurements can be obtained by measuring the radiation received at an optional optical port 206 and provided via at least one optional optical fiber 208. In general, specular signal measurement levels decrease and diffuse signal measurement levels increase when wax particles form in the fuel sample. In some embodiments, the receiver/analyzer 106 uses either of these measurements to determine the cloud point or freeze point of the fuel sample being tested. In particular embodiments, the receiver/analyzer 106 can use a change in one of the specular and diffuse signal measurements to identify the cloud point or freeze point. In other particular embodiments, the receiver/analyzer 106 can use both the specular and diffuse signal measurements to identify the cloud point or freeze point, such as by calculating a ratio or other combination of the two measurements. Note, however, that the cloud point or freeze point of the fuel sample could be calculated in any other suitable manner.

Although FIG. 1 illustrates one example of a fuel cloud point or freeze point sensing system 100 and FIG. 2 illustrates a side view of the example fuel cloud point or freeze point sensing system 100, various changes may be made to FIGS. 1 and 2. For example, the size, shape, and configuration of the sensing cell 102 are for illustration only. Various changes may be made to the sensing cell 102, including those mentioned above. Also, the radiation source 104 and the receiver/analyzer 106 could be combined into a single functional unit, or the receiver/analyzer 106 could be subdivided into separate components.

Figure 3:
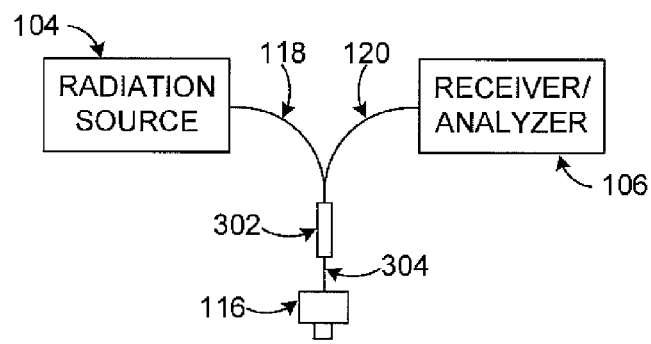
FIG. 3 illustrates an example alternative collinear optical geometry in the fuel cloud point or freeze point sensing system of FIG. 1 according to this disclosure.

FIG. 3 illustrates an example alternative collinear optical geometry in the fuel cloud point or freeze point sensing system 100 of FIG. 1 according to this disclosure. In particular, FIG. 3 illustrates another way that the optical fibers 118-120 could be coupled to the optical port 116 of the sensing cell 102.

In this example, the optical fibers 118-120 are not coupled directly to the optical port 116 of the sensing cell 102. Rather, the optical fibers 118-120 are coupled to a connector 302, which is coupled to the optical port 116 by a single optical fiber 304. In this example, the radiation source 104 and the receiver/analyzer 106 are coupled to the optical port 116 using a bifurcated optical fiber structure. The optical fibers 118-120 couple the components 104-106 to the connector 302. The connector 302 allows radiation from the optical fiber 118 to enter the optical fiber 304 for delivery to the optical port 116. The connector 302 also allows radiation reflected from the mirror 122 and traveling through the optical fiber 304 to be provided to the receiver/analyzer 106. The connector 302 includes any suitable structure for providing radiation from a source to an optical fiber and providing radiation from the optical fiber to a destination. The optical fiber 304 includes any suitable optical fiber.

Although FIG. 3 illustrates one example of an alternative collinear optical geometry in the fuel cloud point or freeze point sensing system 100, various changes may be made to FIG. 3. For example, any other suitable collinear optical geometry could be used in the fuel cloud point or freeze point sensing system 100.

Figure 4:
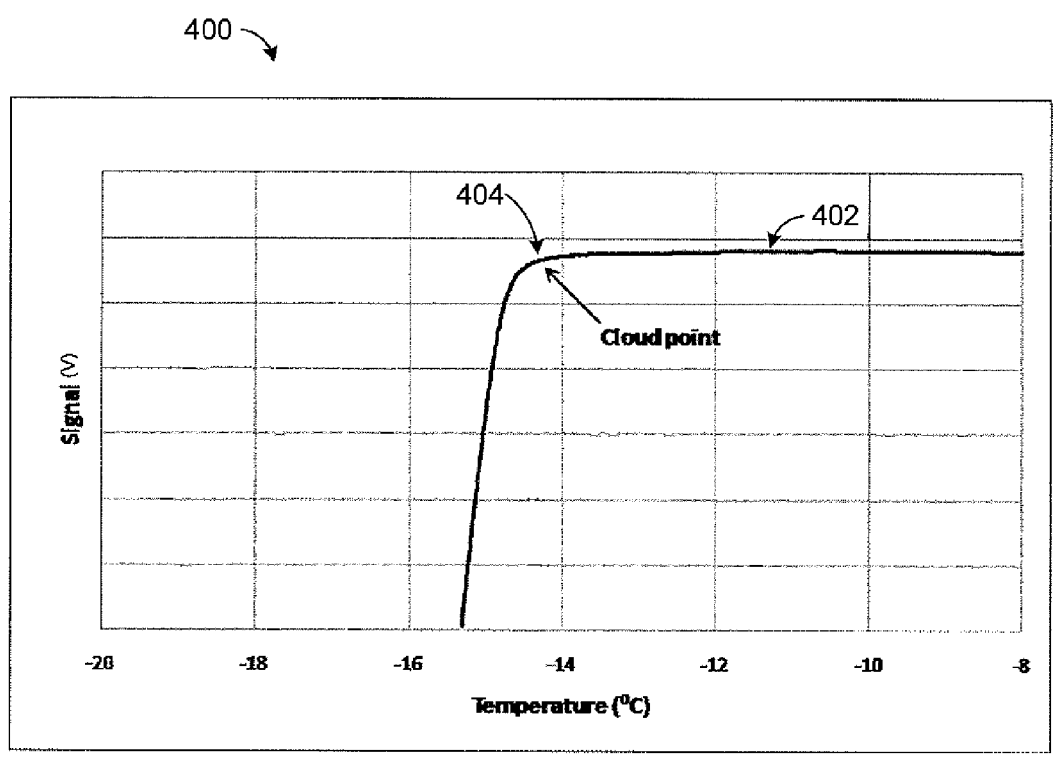
FIGS. 4 and 5 illustrate example measurements using the fuel cloud point or freeze point sensing system of FIG. 1 according to this disclosure.
Figure 5:
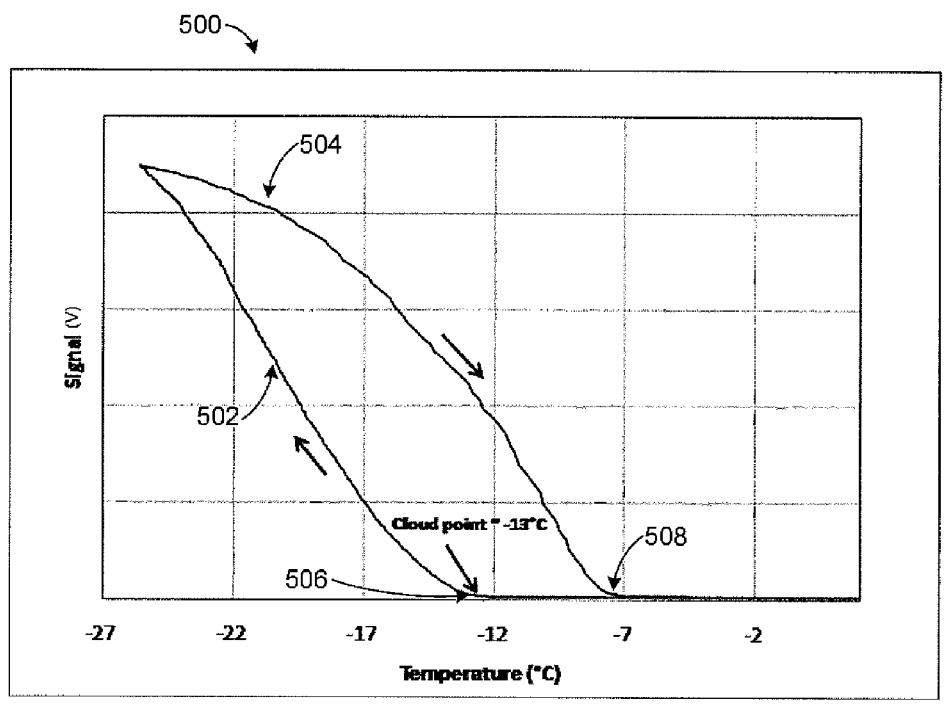

FIGS. 4 and 5 illustrate example measurements using the fuel cloud point or freeze point sensing system 100 of FIG. 1 according to this disclosure. In FIG. 4, a graph 400 is associated with example specular measurements of a fuel sample being cooled. A line 402 plots a temperature of the fuel sample versus the strength of the received radiation. In this example, the received radiation is converted into a voltage signal.

As shown here, the line 402 remains relatively steady as the temperature of the fuel sample drops from around −8° C. to around −14° C. Around a point 404 corresponding to about −15° C., the line 402 begins dropping rapidly. As noted above, specular measurements decrease when wax particles form in the fuel sample. The wax particles significantly reduce the amount of radiation that passes uninterrupted through the fuel sample from the optical port 116 to the mirror 122 and back to the optical port 116 along the optical path 202 in FIG. 2. The receiver/analyzer 106 can process the signal measurements while the fuel sample is cooling and identify the cloud point as being at or near the point 404. For instance, the receiver/analyzer 106 can identify the point 404 where the signal measurements drop by 20%-30% from a baseline value.

In FIG. 5, a graph 500 is associated with example diffuse measurements of a fuel sample being cooled and then warmed. Lines 502-504 plot a temperature of the fuel sample versus the strength of the received diffuse radiation. More specifically, line 502 plots a temperature of the fuel sample versus the strength of the received diffuse radiation as the fuel sample is being cooled, and line 504 plots the temperature of the fuel sample versus the strength of the received diffuse radiation as the fuel sample is being warmed. In this example, the received radiation is converted into a voltage signal. In many cases, the cloud point itself is not measured when the freeze point is being determined. Instead, the fuel is cooled to a point well below its cloud point and then warmed to identify the freeze point (although both cloud point and freeze point could be identified). In the following discussion, it is assumed that the sensing system 100 is not attempting to determine the cloud point when measuring the freeze point.

As shown here, the line 502 remains relatively steady as the temperature of the fuel sample drops from around 0° C. to around −13° C. Around a point 506 corresponding to about −13° C., the line 502 begins increasing rapidly. As noted above, diffuse measurements increase when wax particles form in the fuel sample. The wax particles cause the radiation from the optical port 116 to diffuse within the fuel sample, such as along the path 204 in FIG. 2. At some point (either by default or when detected by the sensing system 100), the fuel sample is below its cloud point, and the sensing system 100 begins warming the fuel sample as shown by line 504. The fuel sample can be warmed either by stopping the cooling of the fuel sample or actually warming the fuel sample. During this time, the strength of the diffuse radiation measurements can decrease as the wax particles in the fuel sample melt. Around a point 508, the diffuse measurements approach approximately zero, indicating that little diffusion is now occurring. The receiver/analyzer 106 can process the signal measurements while the fuel sample is warming and identify the freeze point as being at or near the point 508 where the diffuse measurements are approximately zero. For instance, the receiver/analyzer 106 can identify the point 508 where the signal measurements are within 20%-30% of a baseline value.

Although FIGS. 4 and 5 illustrate examples of measurements using the fuel cloud point or freeze point sensing system 100, various changes may be made to FIGS. 4 and 5. For example, FIGS. 4 and 5 illustrate two example techniques that can be used by the sensing system 100 to determine the cloud point or freeze point of a fuel sample. Any other suitable technique(s) could be used to determine the cloud point or freeze point of a fuel sample. As a particular example, the specular measurements shown in FIG. 4 could also be used during warming of the fuel sample to identify its freeze point. As another particular example, a ratio or other combination of specular and diffuse measurements could be used to identify a fuel to determine the cloud point or freeze point of a fuel sample's cloud point or freeze point.

Figure 6:
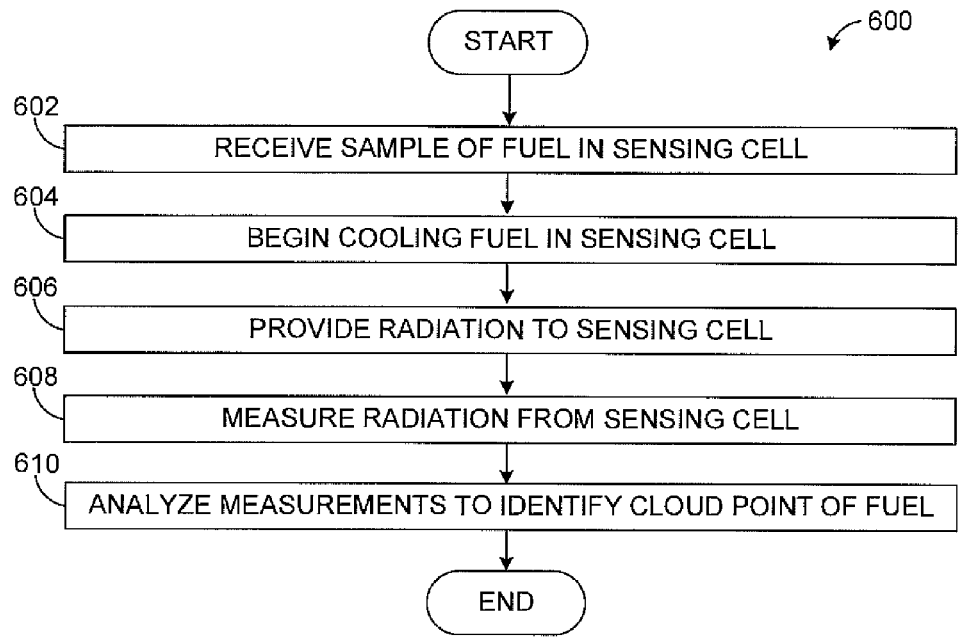
FIGS. 6 and 7 illustrate example methods for cloud point and freeze point measurement according to this disclosure.
Figure 7:
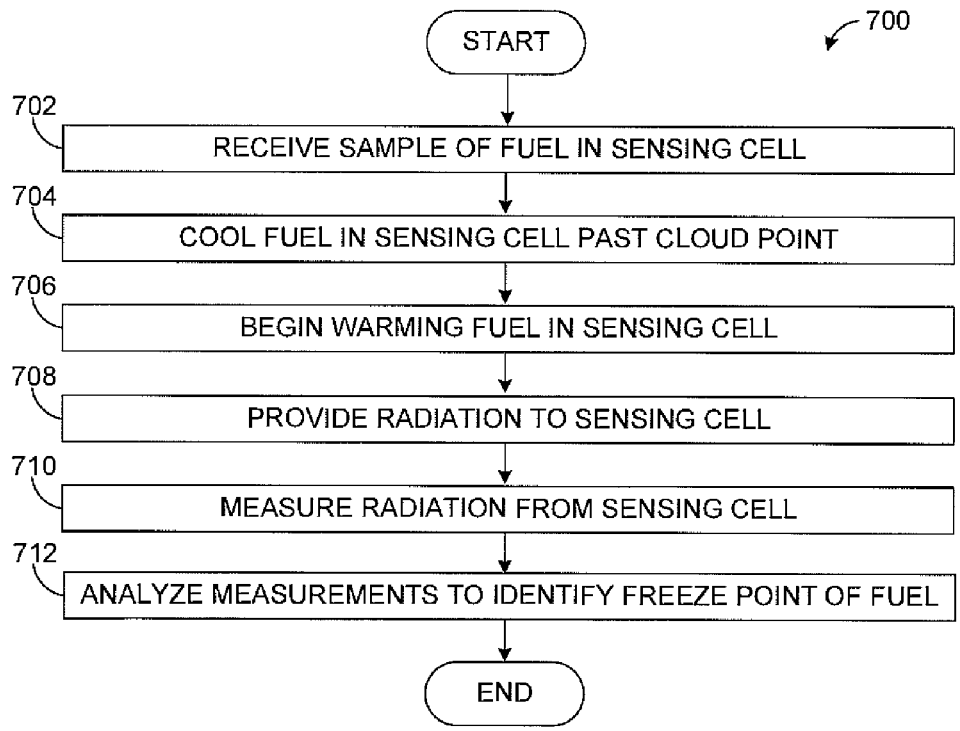

FIGS. 6 and 7 illustrate example methods 600 and 700 for cloud point and freeze point measurement according to this disclosure. As shown in FIG. 6, a sample of fuel is received at a sensing cell at step 602. This could include, for example, operating a pump or opening a valve to allow a sample of fuel being manufactured or processed to enter the sensing cell 102. The fuel sample is cooled at step 604. This could include, for example, the cooler 128 operating to begin lowering the temperature of the fuel sample in the sensing cell 102 via one or more cooling surfaces 124-126.

Radiation is provided to the sensing cell at step 606, and radiation from the sensing cell is measured at step 608. This could include, for example, the radiation source 104 providing visible or other radiation through the optical fiber 118 to the optical port 116 of the sensing cell 102. This could also include the receiver/analyzer 106 measuring visible or other radiation received through the optical fiber 120 from the optical port 116 of the sensing cell 102. Depending on the amount of wax particles or other particles in the fuel sample, the radiation may generally follow a straight path (such as path 202) from the optical port 116 to the mirror 122 and back, or the radiation may generally follow a diverging path (such as path 204) between the optical port 116 and the mirror 122.

The measurements are analyzed to identify the cloud point of the fuel sample at step 610. This could include, for example, the receiver/analyzer 106 using a rapid decrease in specular measurements or a rapid increase in diffuse measurements to identify the cloud point. This could also include the receiver/analyzer 106 using a ratio or other combination of specular and diffuse measurements or using any other signal processing technique to identify the cloud point of the fuel sample in the sensing cell.

At this point, the fuel sample in the sensing cell 102 can be released, and a new fuel sample can be received and tested. A period of time may elapse between tests in order to allow fuel to flow through and warm the sensing cell 102.

As shown in FIG. 7, a sample of fuel is received at a sensing cell at, step 702, and the fuel sample is cooled past its cloud point at step 704. Any suitable technique could be used to cool the fuel sample past its cloud point. For example, the sensing system 100 could cool the fuel sample to a temperature that is assumed to be below its cloud point. The sensing system 100 could also cool the fuel sample and use measurements of the radiation received from the optical port 116 to determine if and when the fuel sample has become cloudy.

The fuel sample in the sensing cell is warmed at step 706. This could include, for example, using a warmer 129 to heat the fuel sample or turning off the cooler 128 and allowing the fuel sample to warm. Radiation is provided to the sensing cell at step 708, and radiation from the sensing cell is measured at step 710. The measurements are analyzed to identify the freeze point of the fuel sample at step 712. This could include, for example, the receiver/analyzer 106 using a rapid increase in specular measurements or a rapid decrease in diffuse measurements to identify the freeze point. This could also include the receiver/analyzer 106 using a ratio or other combination of specular and diffuse measurements or using any other signal processing technique to identify the freeze point of the fuel sample in the sensing cell. At this point, the fuel sample in the sensing cell 102 can be released, and a new fuel sample can be received and tested.

In this way, the sensing system 100 provides on-line sensor capabilities in a fuel manufacturing or processing system. That is, fuel in the manufacturing or processing system can be tested within the system itself in a more real-time manner, rather than capturing a sample of fuel and analyzing the sample some time later in a laboratory.

Although FIGS. 6 and 7 illustrate example methods 600 and 700 for cloud point and freeze point measurement, various changes may be made to FIGS. 6 and 7. For example, while each figure shows a series of steps, various steps in each figure could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   a walled structure configured to receive a fuel sample within an interior space of the walled structure;
   at least one cooling surface located on at least a portion of the walled structure and configured to cool the fuel sample;
   a first optical port positioned on a first wall of the walled structure, the first optical port configured to provide first radiation to the fuel sample;
   a mirror positioned on a second wall of the wall structure opposite from the first wall, the mirror configured to reflect the first radiation in order to provide second radiation to the first optical port; and
   a second optical port positioned on the first wall adjacent to the first optical port, the second optical port configured to receive third radiation reflected by the mirror for diffuse measurements for the fuel sample;
   wherein the first optical port defines a collinear optical geometry for providing the first radiation to the fuel sample and receiving the second radiation through the fuel sample.

2. The apparatus of claim 1, wherein the third radiation is radiation reflected by the mirror and diffused by formation of wax particles in the fuel sample.

3. The apparatus of claim 1, wherein the at least one cooling surface comprises multiple cooling surfaces located on multiple walls of the walled structure.

4. The apparatus of claim 1, wherein the first optical port is configured to receive the second radiation for specular measurements.

5. The apparatus of claim 1, further comprising:
   an inlet configured to receive the fuel sample into the walled structure; and
   an outlet configured to provide the fuel sample from the walled structure.

6. The apparatus of claim 1, wherein the walled structure comprises an insulated walled structure.

7. A system comprising:
   a sensing cell comprising:
      a walled structure configured to receive a fuel sample within an interior space of the walled structure;
      at least one cooling surface located on at least a portion of the walled structure and configured to cool the fuel sample;
      a first optical port positioned on a first wall of the walled structure, the first optical port configured to provide first radiation to the fuel sample;
      a mirror positioned on a second wall of the wall structure opposite from the first wall, the mirror configured to reflect the first radiation in order to provide second radiation to the first optical port; and
      a second optical port positioned on the first wall adjacent to the first optical port, the second optical port configured to receive third radiation reflected by the mirror for diffuse measurements for the fuel sample;
      wherein the first optical port defines a collinear optical geometry for providing the first radiation to the fuel sample and receiving the second radiation through the fuel sample; and
   at least one cooler configured to cool the fuel sample in the sensing cell by cooling the at least one cooling surface.

8. The system of claim 7, wherein the third radiation is radiation reflected by the mirror and diffused by formation of wax particles in the fuel sample.

9. The system of claim 7, wherein the at least one cooling surface comprises multiple cooling surfaces located on multiple walls of the walled structure.

10. The system of claim 7, wherein the cooler comprises one of: one or more Peltier coolers and a cryogenic cooler.

11. The system of claim 7, further comprising:
   a radiation source configured to generate the first radiation; and
   an optical fiber configured to deliver the first radiation from the radiation source to the first optical port.

12. The system of claim 7, further comprising:
an analyzer configured to analyze the second radiation to identify at least one of: a cloud point of the fuel sample and a freeze point of the fuel sample.

13. The system of claim 12, wherein the analyzer is configured to identify at least one of the cloud point of the fuel sample and the freeze point of the fuel sample using one or more of: specular measurements of the second radiation and the diffuse measurements of the third radiation.

14. The system of claim 13, wherein:
the analyzer is configured to determine the cloud point of the fuel sample based on at least one of: a decrease in the specular measurements of the second radiation and an increase in the diffuse measurements of the third radiation; and
the analyzer is configured to determine the freeze point of the fuel sample based on at least one of: an increase in the specular measurements of the second radiation and a decrease in the diffuse measurements of the third radiation.

* * * * *